US007718167B2

(12) United States Patent
Hynes

(10) Patent No.: US 7,718,167 B2
(45) Date of Patent: May 18, 2010

(54) METHOD FOR TREATING WOUNDS EXPOSING THE DURA USING PPP AND PRP

(76) Inventor: Richard A. Hynes, 603 Atlantic St., Melbourne Beach, FL (US) 32951

( * ) Notice: Subject to any disclaimer, the term of this patent is extended or adjusted under 35 U.S.C. 154(b) by 509 days.

(21) Appl. No.: 11/225,139

(22) Filed: Sep. 13, 2005

(65) Prior Publication Data

US 2006/0057224 A1 Mar. 16, 2006

Related U.S. Application Data

(60) Provisional application No. 60/609,528, filed on Sep. 13, 2004.

(51) Int. Cl.
*A01N 63/00* (2006.01)
(52) U.S. Cl. .................................. 424/93.72
(58) Field of Classification Search ................ None
See application file for complete search history.

(56) References Cited

U.S. PATENT DOCUMENTS

| 5,607,694 | A | * | 3/1997 | Marx | 424/450 |
|---|---|---|---|---|---|
| 5,887,755 | A | * | 3/1999 | Hood, III | 222/135 |
| 5,997,895 | A | * | 12/1999 | Narotam et al. | 424/423 |
| 6,524,568 | B2 | * | 2/2003 | Worden | 424/78.06 |
| 6,649,072 | B2 | | 11/2003 | Brandt et al. | 210/782 |
| 6,719,901 | B2 | * | 4/2004 | Dolecek et al. | 210/380.1 |
| 2002/0009500 | A1 | | 1/2002 | Wolkers et al. | 424/532 |
| 2002/0159985 | A1 | | 10/2002 | Baugh et al. | 424/93.72 |
| 2003/0007957 | A1 | | 1/2003 | Britton et al. | 424/93.72 |
| 2003/0152639 | A1 | | 8/2003 | Britton et al. | 424/529 |
| 2003/0185812 | A1 | | 10/2003 | Ferree | 424/93.72 |
| 2003/0194397 | A1 | | 10/2003 | Mishra | 424/93.72 |
| 2004/0001816 | A1 | | 1/2004 | Worden | 424/93 |

OTHER PUBLICATIONS

Soffer et al., "Fibrin sealants and platelet preparations in bone and periodontal healing", Oral Surg., Oral Med., Oral Pathol., Oral Radiol. Endod. 95: 521-528 (2003).*

Whitman et al., "Platelet Gel: An Autologous Alternative to Fibrin Glue With Applications in Oral and Maxillofacial Surger", J. Oral Maxillofacial Surgery 55: 1294-1299 (1997).*
Robertson et al., "Prevention of Cerebrospinal fistulae and Reduction of Epidural Scar with New Surgical Hemostat Device in a Porcine Laminectomy Model", Spine 28 (19) : 2298-2303 (2003).*
Vaquero et al., "Effect of Fibrin Glue on Postlaminectomy Scar Formation", Acta neurochir (Wien) 120: 159-163 (1993).*
Ozkan et al., "Widespread post-traumatic acute spinal subdural haematoma case report and review of the literature", Spinal Cord 40 : 304-306 (2002).*
"The Use of Autologous Platelet-Rich Plasma (Platelet Gel) and Autologous Platelet-Poor Plasma (Fibrin Glue) in Cosmetic Surgery', Man et al., Plastic and Reconstructive Surgery", Jan. 2001, vol. 107, No. 1, pp. 229-237, XP009060962, ISSN: 0032-1052.
"Using Platelet-rich Plasma to Accelerate Soft Tissue Maturation in Esthetic Periodontal Surgery", Petrungano, Compendium of Continuing Education in Dentistry (Jamesburg, N.J. :1995) Sep. 2001, vol. 22, No. 9, pp. 1-10, XP002365742, ISSN: 1548-8578.
Tözüm et al., *Platelet-Rich Plasma: A Promising Innovation in Dentistry*, Journal of the Canadian Dental Association, Nov. 2003, vol. 69, No. 10, pp. 664-664h.
Tischler, *Platelet Rich Plasma-Utilizing Autologous Growth Factors for Dental Surgery to Enhance Bone and Soft Tissue Grafts*, New York State Dental Journal, Mar. 2002, available at http://www.tischlerdental.com/pdf/PRPNYS_3-02.pdf.
*Platelet Gel Transcript*, OhioHealth; 2004, available at http://www.ohiohealth.com/body.cfm?id=181.
*Shoulder Recovery with the GPS Platelet Concentrate System*, Biomet International, 2004, available at http://www.biomet.com/biologics/international/print/gps_shoulder.pdf.

* cited by examiner

*Primary Examiner*—Sandra E Saucier
(74) *Attorney, Agent, or Firm*—Allen, Dyer, Doppelt, Milbrath & Gilchrist, P.A.

(57) ABSTRACT

A method for treating an open wound, such as a surgical wound, may include preparing a first composition including a platelet poor plasma (PPP), and preparing a second composition including a platelet rich plasma (PRP). A layer of the first composition may be applied within the open wound, and a layer of the second composition may be applied within the open wound over the layer of the first composition.

12 Claims, 5 Drawing Sheets

METHOD FOR TREATING WOUNDS EXPOSING THE DURA USING PPP AND PRP

CROSS-REFERENCE TO RELATED APPLICATIONS

This application claims the benefit of U.S. Provisional Application No. 60/609,528, filed Sep. 13, 2004, which is hereby incorporated herein in its entirety by reference.

FIELD OF THE INVENTION

The present invention relates to the field of surgery, and, more particularly, to surgical techniques to promote wound healing and related methods.

BACKGROUND OF THE INVENTION

In recent years it has been discovered that the use of platelet rich plasma (PRP) in a wound, such as a surgical wound, can provide enhanced bone and soft tissue regeneration, and thus faster healing times. PRP is an autologous source for growth factors obtained from a sample of a patient's blood. The sample is processed in a centrifuge, which separates the platelets from the blood to provide both a PRP and a platelet poor plasma (PPP). One example of a centrifuge used for platelet separation is the GPS platelet concentration system from Cell Factor Technologies, Inc (CFT). Not only can the PRP have medicinal use, but CFT notes in a publication entitled "Shoulder Recovery with the CPS Platelet Concentrate System" that PPP may be sprayed on the exterior of an incision to act as a fibrin sealant at closure.

Given the advantageous healing properties of PRP, various approaches have accordingly been developed for its processing and use. For example. U.S. Pat. No. 6,649,072 to Brandt et al. discloses a method for producing an autologous PRP blood composition. The method includes combining PRP and PPP components which have been centrifugally separated from whole blood drawn from a patient. These two components are combined in a desired ratio to create a composition useful in surgical bone growth enhancement, soft tissue repair procedures, and as an aid in controlling surgical and traumatic hemostasis. In particular, the PPP is concentrated to provide a coagulum that is useful in bonding together various bone fragments or bone fusion products, as well as providing a tighter matrix or scaffold for enticing the migration of osteoblasts and for the enhancement of hemostasis.

U.S. pat. Pub. No. 2002/0009500 to Wolkers et al. is directed to a dehydrated composition that includes freeze-dried platelets and one or more other agents, such as antibiotics, antifungals, and growth factors. The composition may also be placed on a biocompatible surface to provide a hemostasis aid. The Wolkers et al. publication notes that the drug-loaded platelets are particularly intended for use with blood-borne drug delivery, such as where the selected drug is targeted to a site of platelet-mediated forming thrombi or vascular injury.

Despite such advancements in wound treatment, further advancements may be desirable in certain applications.

SUMMARY OF THE INVENTION

In view of the foregoing background, it is therefore an object of the present invention to provide treatment methods to promote wound healing.

This and other objects, features, and advantages in accordance with the present invention are provided by a method for treating an open wound, such as a surgical wound, for example. The method may include preparing a first composition comprising a platelet poor plasma (PPP), and preparing a second composition comprising a platelet rich plasma (PRP). Furthermore, a layer of the first composition is applied within the open wound, and a layer of the second composition is also applied within the open wound over the layer of the first composition. By way of example, one particular application for the wound treatment method is for treating a surgical wound of a patient resulting from spinal surgery that exposes the patient's dura. The method may also be used for treating numerous other types of wounds as well.

At least one of the first and second compositions may include a medication such as an analgesic and/or an antibiotic. The PPP dissolves and is reabsorbed by the body within a relatively short time, while the PRP takes longer (i.e., a few weeks) to dissolve. Thus, when antibiotics are used in the first and second compositions, for example, the first layer of the PPP/antibiotic composition provides initial infection treatment. However, the layer of the second composition including the PRP may be shape-retaining or settable. Thus, when the PPP is dissolved a small void (e.g., less than about 3 mm) remains, in the case of a surgical spinal wound, between the dura and the second layer including the PRP. This provides a close approximation of the original dural space, and this void may advantageously reduce the amount of scar tissue that is formed on the dura, for example. The second layer may continue to promote healing and infection prevention thereafter.

The layer of the second composition may have a thickness of less than about 4 mm, for example. The method may further include closing the open wound after applying the layer of the second composition, e.g., using sutures. Moreover, a PPP sealant layer may advantageously be applied over the wound closed to help keep the wound closed and prevent infections.

Another method aspect for treating an open wound exposing an element of a patient's nervous or musculoskeletal system may include applying a layer of a first biocompatible material within the open wound on the exposed element, and applying a layer of a second shape-retaining biocompatible material in the open wound over the layer of the first composition. The first biocompatible material may dissolve more rapidly in the open wound than the second shape-retaining biocompatible material to thereby upon dissolving leave a void between the exposed element and the layer of second biocompatible material.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Referring to FIGS. 1 through 5, the present invention is directed to a wound treatment method which may advantageously reduce the occurrence of scarring around nerves, joints, bones, etc. In particular, the method is particularly well suited for use in a surgical wound 40 in a patient 41 that exposes an element 42 of the patient's musculoskeletal or nervous system. By "exposing" the element 42 it is meant that the wound 40 extends at least to the element, although some spinal procedures will require relatively deep wounds extending past the element to access underlying bones, nerves, ligaments, etc., as will be appreciated by those skilled in the art. However, the present invention may be used with numerous types of open wounds at different locations throughout a human or animal body, and the wound need not be the result of a surgical incision, as will also be appreciated from the description below.

Figure 1:
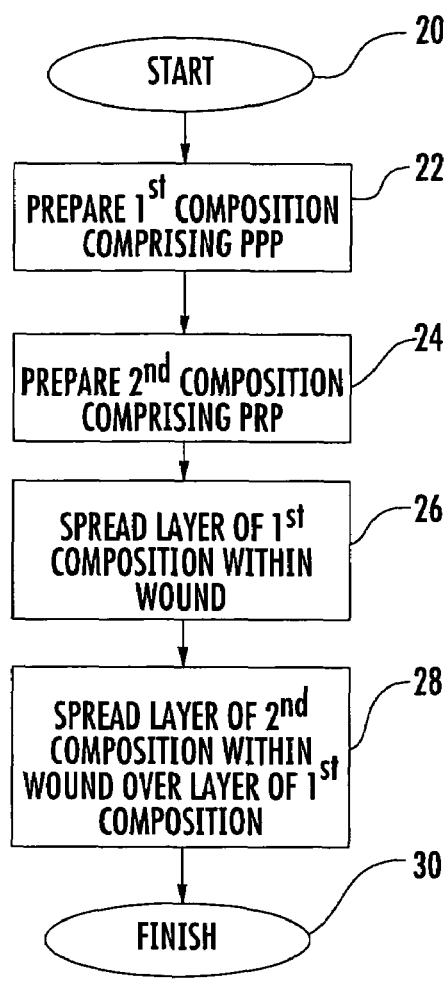
FIGS. 1 and 2 are flow diagrams of wound treatment methods in accordance with the present invention.
Figure 2:
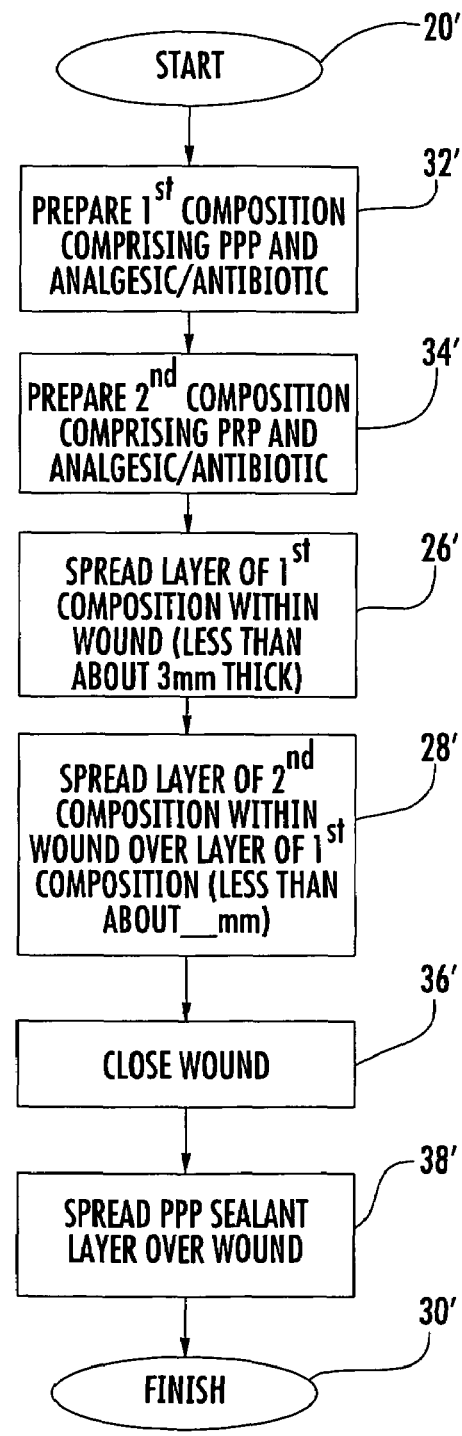
Figure 3:
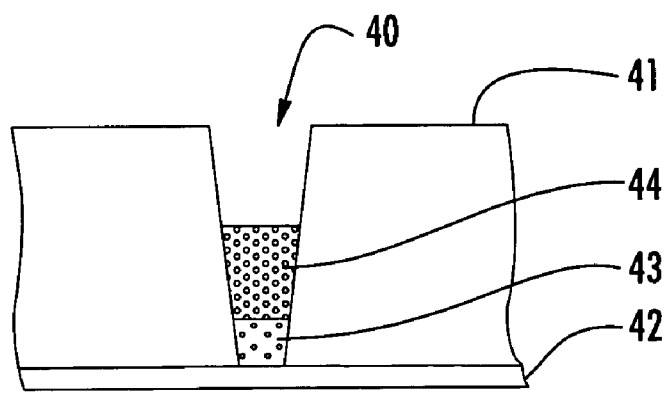
FIGS. 3-5 are schematic cross-sectional views of a wound illustrating the method of FIG. 1 during the application of PPP and PRP composition layers, after closing of the wound, and after the PRP composition layer is absorbed by the patient's body, respectively.
Figure 4:
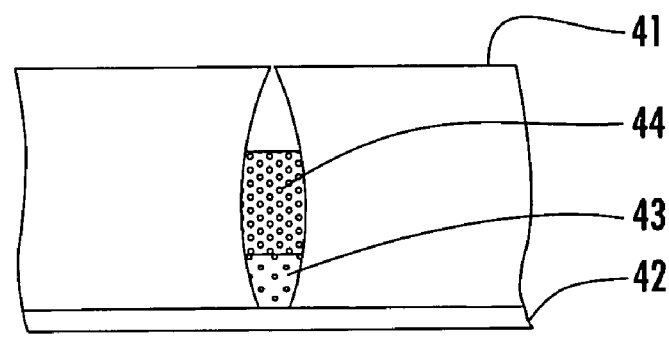

Beginning at Block 20 of the flowchart of FIG. 1, the method may include preparing a first composition including a platelet poor plasma (PPP), at Block 22, and preparing a second composition including a platelet rich plasma (PRP), at Block 24. The PRP/PPP materials may be prepared using various techniques and/or devices known to those skilled in the art, such as the above-noted GPS platelet concentrate system, for example. The first and/or second compositions may also include antibiotics to help prevent infections and/or analgesics, at Blocks 32' and 34' (FIG. 2). Other medications may also be included to help control pain, prevent infection, prevent scar tissue, etc., as will be appreciated by those skilled in the art.

The method further illustratively includes applying or spreading a layer 43 of the first composition within the open wound 40, at Block 26, and then applying a layer 44 of the second composition within the open wound over the layer of the first composition (FIG. 3), at Block 28, thus concluding the method illustrated in FIG. 1 (Block 30). By way of example, in the case of spinal surgery, the first layer 43 of the PPP composition is preferably spread over the dura to a thickness of less than about 3 mm, and more particularly about 1-2 mm, the approximate thickness of the original dural space. The second layer 44 of the PRP composition may be less than about 4 mm thick for this application, and more particularly about 2-3 mm. It should be noted, however, that different layer thicknesses may be used in different embodiments or applications, as will be appreciated by those skilled in the art.

Figure 5:
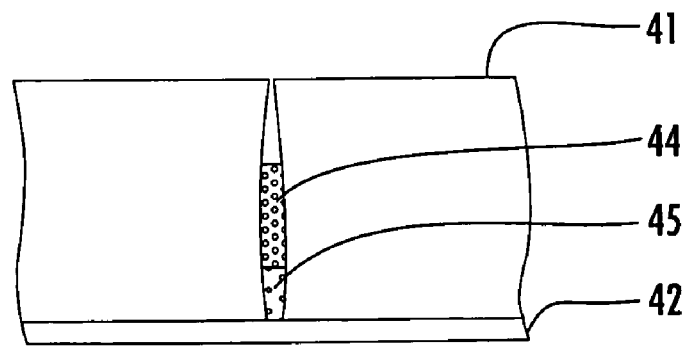

Preferably, the PRP and/or PPP materials are settable or shape-retaining so that they do not mix together, and thus form separate and distinct layers 43, 44 that remain in place until they dissolve. The PPP dissolves relatively quickly (i.e., within a few days) and is reabsorbed by the body, while the PRP may take longer (i.e., a few weeks) to dissolve and be reabsorbed. As such, the layer 43 of the PPP composition provides initial infection/pain treatment, yet when the PPP composition is dissolved a small void or gap 45 remains between the element 42 and the second layer 44 of PRP (FIG. 5). In the case of spinal surgery, this provides a close approximation of the original dural space. Applicants theorize, without wishing to be bound thereto, that the void 45 will help reduce the amount of scar tissue that is formed on or adjacent the element 42. The PRP/antibiotic layer 44 continues to promote healing and possibly infection prevention for the next several weeks while the wound 40 continues to heal.

Accordingly, the layer 43 of the PPP composition is advantageously used as a barrier to the in-growth of scar tissue among the nerves in the epidural space, for example, which may result in less post-operative pain for patients. Stated alternately, this prevents scar tissue and tethering of the dura 42 and nerves after surgery, such as laminectomy surgery, for example. Here again, this technique may be used to provide an in-growth scar tissue barrier to other elements of the musculoskeletal or nervous system in a similar manner, as will be appreciated by those skilled in the art. PPP may also be used as a sealant upon closure of the wound (FIG. 4), if desired, as illustrated at Blocks 36' and 38'.

Of course, in some applications the wound may be the result of a puncture (e.g., an epidural procedure) and not an incision, in which case wound closure with sutures, etc., need not necessarily be used (i.e., a wound dressing, adhesive bandage, and/or PPP sealant may be sufficient). It should also be noted that the above-described method is not limited to surgical wounds, and it may also be used in some circumstances for treating other types of wounds resulting from cuts or punctures, as will be appreciated by those skilled in the art.

While PPP and PRP have been discussed above as the base materials for the layers 43, 44 to be applied to the element 42, those skilled in the art will appreciate that other suitable biocompatible materials whether biological, chemical, and/or synthetic may be used in accordance with the present invention to re-create the dural space and thus provide a barrier to scar in-growth, as discussed above. Other applications in which the above-noted approach is particularly well suited are for portions of the body where movement occurs, such as over a joint or bony surface where it is desirable to create a space to allow residual movement, thereby in effect providing a bursae to reduce tethering.

It should also be noted that the antibiotic or other medication may be used not only to reduce the likelihood of infection or pain, but it may also be used to titrate the rate of breakdown of the PPP (or PRP) composition, for example, if needed. One exemplary antibiotic which may be used is vancomycin, although other suitable antibiotics may be used as well. Moreover, other carriers or biocompatible materials may be used in the compositions to change the viscosity, setting properties, etc., of the PPP and/or PRP compositions as appropriate for a given application.

Figure 6:
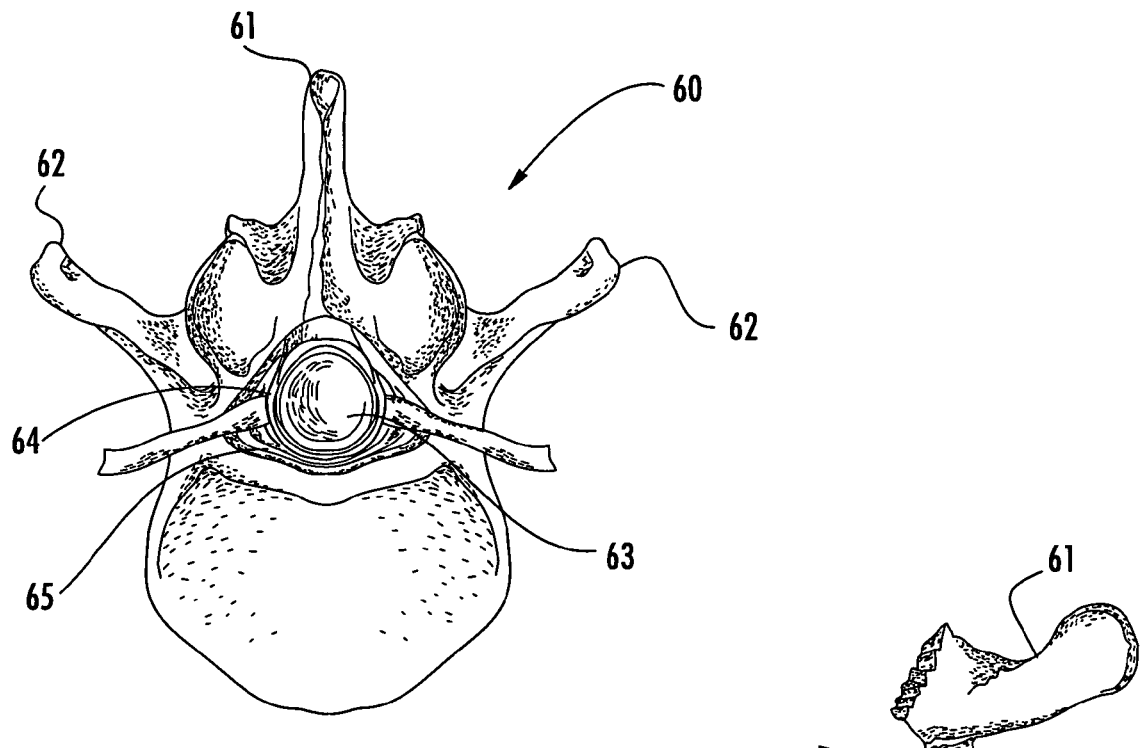
FIGS. 6-12 are a series of perspective views of a vertebra illustrating further method aspects of the present invention.
Figure 7:
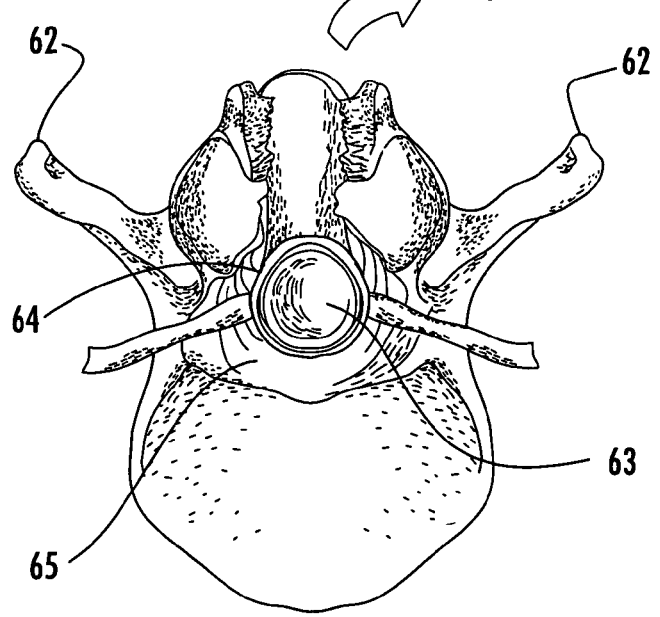

Another particularly advantageous implementation for spinal surgery will now be described with reference to FIGS. 6-12. This implementation may be used to create a potential space beneath a dural barrier 68 (FIG. 10) and above the dura 64. A vertebra 60 having a spinous process 61 and pedicles 62 is shown in FIG. 6 prior to surgery. The spinal cord 63 is surrounded by the dura 64 within the epidural space 65. In the present example, the epidural space 65 and spinal cord 63 are accessed by performing a laminectomy to remove the spinous process 61 and lamina, as seen in FIG. 7. A laminectomy may be required for various reasons, such as to alleviate disc herniation or spinal canal stenosis, for example.

Figure 8:
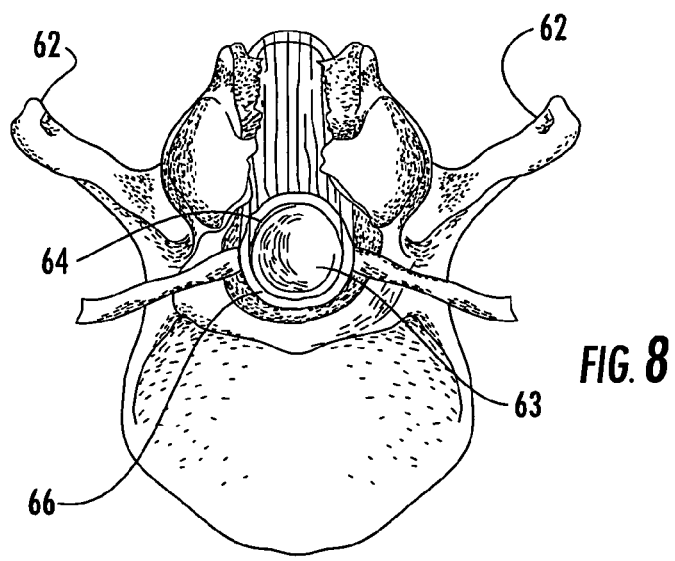
Figure 9:
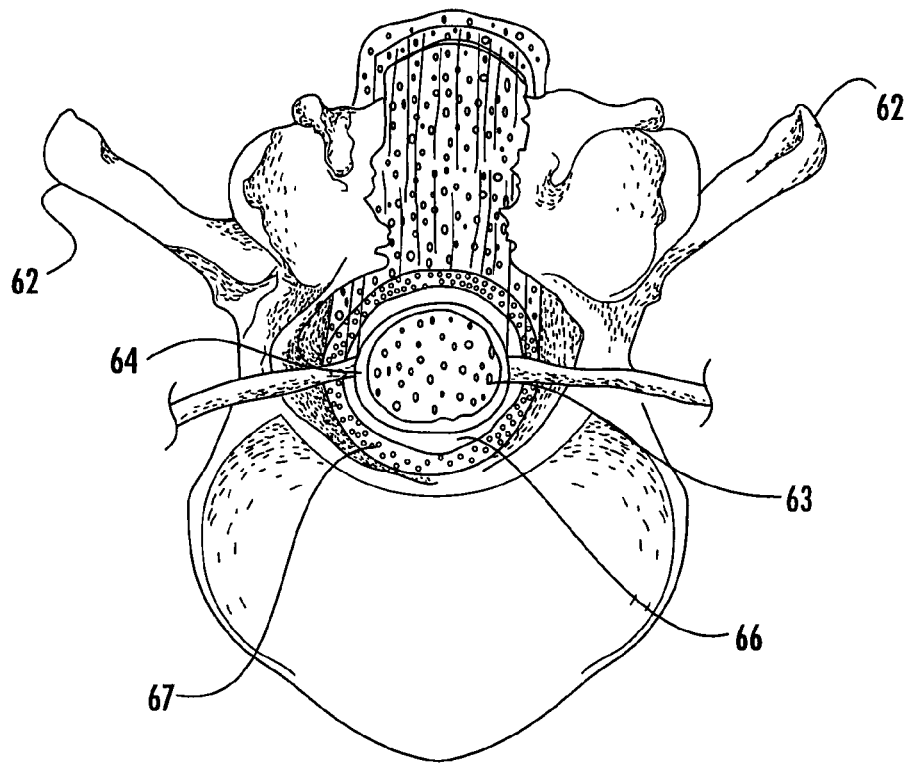

Once the desired surgical procedure has been completed, a layer 66 of the above-described PPP composition is applied within the epidural space 65 substantially surrounding the dura 64, as shown in FIG. 8. A layer 67 of the above-described PRP composition is also applied within the epidural space 65 substantially surrounding the layer 66 of the PPP composition, as seen in FIG. 9.

Figure 10:
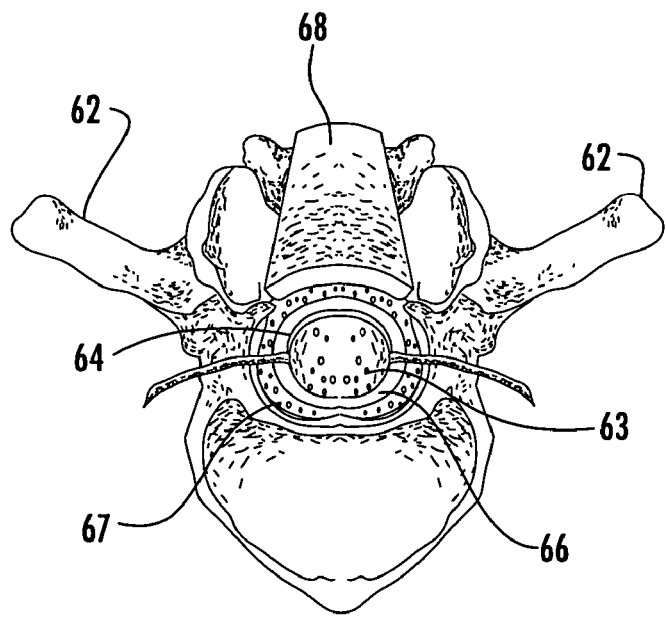
Figure 12:
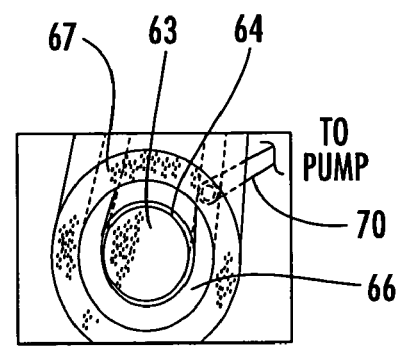
Figure 11:
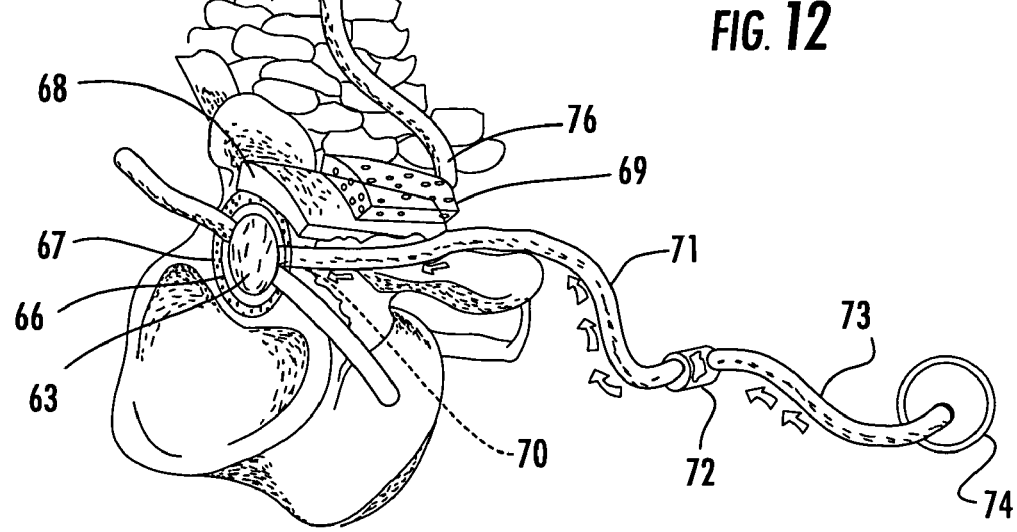

As illustrated in FIGS. 10 through 12, a relatively small diameter irrigation catheter 70 is then positioned in the epidural space 65 to extend through the layer 67 of the PRP composition into the layer 66 of the PPP composition. The irrigation catheter 70 is connected via a tube 71 to a one-way valve/pump 72, which in turn is connected via a tube 73 to a fluid dispensing reservoir 74. The irrigation catheter 70 thus advantageously allows fluid from the fluid dispensing reservoir 74 to be introduced over time into the epidural space 65 as the layers 66 and 67 breakdown and are reabsorbed. The valve/pump 72 is typically located externally to the patient's skin.

Once the irrigation catheter 70 is in place, the dural barrier 68 may then be positioned over the layer 67 of the PRP composition, followed by another layer 69 of the PRP composition, if desired. The dural barrier 68 is typically a synthetic collagen material used for replacing the lamina bone, as will be appreciated by those skilled in the art.

The fluid is pumped through the irrigation catheter 70 to provide a hydraulic force for "pushing" the breakdown products out of the epidural space 65 as they accumulate during the postoperative period. The one-way valve senses pressure changes and maintains a constant pressure and slow elution of fluid into the epidural space 65. The fluid eventually will surround the dura 64 in a "bath," and it will eventually be reabsorbed by the venous and lymphatics of the epidural space 65.

Some of the fluid may also seep out around the edges of the semi-constrained dural barrier 68. This would then result in the fluid collecting "above" the dural barrier 68, i.e., outside of the epidural space 65 and under the back muscle. As such, in some applications it may be desirable to place a drain catheter 76 in the wound to collect any such seepage. The drain catheter 76 may be connected to a collection reservoir (not shown) via a tube 77. By way of example, one particularly advantageous catheter configuration which may be used for this purpose is disclosed in co-pending application Ser. No. 11/150,512, filed Jun. 10, 2005, which is hereby incorporated herein in its entirety by reference. This catheter system may advantageously be used to release antibiotics or other medicines while at the same time collecting the seepage and other wound healing byproducts (e.g., blood and seroma) and evacuating them to the collection reservoir to be discarded. Of course, other evacuation catheters may also be used.

The fluid from the fluid dispensing reservoir 74 may be used not only for its hydraulic properties, but also for medicinal purposes. By way of example, the fluid may include one or more of antibiotics, analgesics or pain medication, steroids, heparin, or other medicines based upon the particular goals of the surgeon and needs of the patient, as will be appreciated by those skilled in the art. Thus, the irrigation catheter 70 may be used to dispense numerous types of medicines to aid in preventing infection, give postoperative analgesia, and/or introduce other medicines/chemicals to help prevent the formation of scar tissue which can lead to permanent nerve damage and pain, for example.

By the time the PPP and PRP compositions have washed out or been reabsorbed within the epidural space 65, the post-operative ingrowth of healing cells and factors may be ending, which may in turn stop the biological process of scar formation. The result of the above-noted procedures may therefore leave the patient with a "new" epidural space 65 allowing for expansion of the dura 64 with the cerebrospinal fluid (CSF) internal fluid pump in tact, and allowing greater movement of nerve roots because they are not tethered down in scar tissue.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method for treating a surgical wound of a patient which exposes the patient's dura comprising:
    preparing a first composition from a platelet poor plasma (PPP);
    preparing a second composition from a platelet rich plasma (PRP);
    applying a layer of the first composition, which is settable or shape-retaining, within the surgical wound on the patient's dura; and
    applying a layer of the second composition which is shape-retaining within the surgical wound and over the layer of the first composition, whereby the first and second compositions form separate and distinct layers.

2. The method of claim 1 wherein at least one of the first and second compositions further comprises an analgesic.

3. The method of claim 1 wherein at least one of the first and second compositions further comprises an antibiotic.

4. The method of claim 1 wherein the applied layer of the first composition has a thickness of less than 3 mm.

5. The method of claim 1 wherein the applied layer of the second composition has a thickness of less than 4 mm.

6. The method of claim 1 further comprising closing the surgical wound after applying the layer of the second composition.

7. The method of claim 6 further comprising applying a PPP sealant layer over the closed wound.

8. The method of claim 1 wherein applying the layer of the first composition comprises applying the layer of the first composition within an epidural space substantially surrounding the dura.

9. The method of claim 8 wherein applying the layer of the second composition comprises applying the layer of the second composition within an epidural space substantially surrounding the layer of the first composition.

10. The method of claim 1 further comprising placing a dural barrier within the surgical wound over the layer of the second composition.

11. The method of claim 10 wherein the dural barrier comprises collagen.

12. The method of claim 1 further comprising positioning an irrigation catheter within the surgical wound for irrigating the epidural space of the patient.

* * * * *